US008992914B2

(12) United States Patent
Weaver et al.

(10) Patent No.: US 8,992,914 B2
(45) Date of Patent: Mar. 31, 2015

(54) WATER-SOLUBLE GLOBULIN CONCENTRATE FOR IMPROVING GROWTH IN ANIMALS

(75) Inventors: Eric M. Weaver, Story City, IA (US); Daniel U. Thomson, Ames, IA (US)

(73) Assignee: APC, Inc., Ankeny, IA (US)

( * ) Notice: Subject to any disclaimer, the term of this patent is extended or adjusted under 35 U.S.C. 154(b) by 712 days.

(21) Appl. No.: 11/926,470

(22) Filed: Oct. 29, 2007

(65) Prior Publication Data
US 2008/0112948 A1 May 15, 2008

Related U.S. Application Data

(63) Continuation of application No. 10/613,633, filed on Jul. 3, 2003, now abandoned, which is a continuation of application No. 09/659,103, filed on Sep. 11, 2000, now abandoned, which is a continuation-in-part of application No. 09/258,553, filed on Feb. 26, 1999, now abandoned, which is a continuation-in-part of application No. 09/210,490, filed on Dec. 11, 1998, now abandoned.

(51) Int. Cl.
| | | |
|---|---|---|
| A61K 39/395 | (2006.01) |
| A23K 1/18 | (2006.01) |
| A23K 1/00 | (2006.01) |
| A23K 1/04 | (2006.01) |
| C07K 16/06 | (2006.01) |
| A61K 39/00 | (2006.01) |

(52) U.S. Cl.
CPC ............... *A23K 1/184* (2013.01); *A23K 1/001* (2013.01); *A23K 1/04* (2013.01); *A23K 1/18* (2013.01); *A23K 1/1813* (2013.01); *A23K 1/1826* (2013.01); *A23K 1/1893* (2013.01); *C07K 16/06* (2013.01); *A61K 2039/505* (2013.01)
USPC ........................................................ 424/133.1

(58) Field of Classification Search
None
See application file for complete search history.

(56) References Cited

U.S. PATENT DOCUMENTS

| | | | |
|---|---|---|---|
| 4,096,244 A | 6/1978 | Newson et al. |
| 4,623,541 A | 11/1986 | Elliot et al. |
| 4,816,252 A | 3/1989 | Stott et al. |
| 5,017,372 A * | 5/1991 | Hastings .................... 424/157.1 |
| 5,143,257 A | 9/1992 | Austin et al. |
| 5,372,811 A | 12/1994 | Yoder |
| 5,531,988 A * | 7/1996 | Paul ............................ 424/93.4 |

FOREIGN PATENT DOCUMENTS

JP          61132143          6/1986

OTHER PUBLICATIONS

Websters II New Riverside University Dictionary, 1988, p. 1307.*
"U.S. Appl. No. 10/613,633 Response to Non-Final Office Action filed Mar. 20, 2008", 12 pgs.
"U.S. Appl. No. 10/613,633 Final Office Action mailed Jun. 16, 2008", FOAR, 9 pgs.
"U.S. Appl. No. 09/659,103 Final Office Action mailed Feb. 7, 2003", 7 pgs.
"U.S. Appl. No. 09/659,103 Non-Final Office Action mailed May 20, 2002", 6 pgs.
"U.S. Appl. No. 09/659,103 Response to Non-Final Office Action filed Nov. 19, 2002", 15 pgs.
"U.S. Appl. No. 10/613,633 Final Office Action mailed Jan. 24, 2006", 6 pgs.
"U.S. Appl. No. 10/613,633 Final Office Action mailed Jan. 4, 2007", 7 pgs.
"U.S. Appl. No. 10/613,633 Non-Final Office Action mailed May 2, 2005", 7 pgs.
"U.S. Appl. No. 10/613,633 Non-Final Office Action mailed Jun. 29, 2006", 10 pgs.
"U.S. Appl. No. 10/613,633 Non-Final Office Action mailed Sep. 20, 2007", 7 pgs.
"U.S. Appl. No. 10/613,633 Response to Final Office Action filed Feb. 23, 2006", 6 pgs.
"U.S. Appl. No. 10/613,633 Response to Final Office Action filed Apr. 18, 2006", 6 pgs.
"U.S. Appl. No. 10/613,633 Response to Final Office Action filed Apr. 4, 2007", 8 pgs.
"U.S. Appl. No. 10/613,633 Response to Non-Final Office Action filed Nov. 2, 2005", 9 pgs.
"U.S. Appl. No. 10/613,633 Response to Non-Final Office Action filed Sep. 26, 2006", 9 pgs.

* cited by examiner

*Primary Examiner* — Yunsoo Kim
(74) *Attorney, Agent, or Firm* — Schwegman Lundberg & Woessner, P.A.

(57) ABSTRACT

A water soluble globulin concentrate is described. The globulin concentrate is administered through the animals' water supply and is effective in increasing growth and weight gain in animals. The concentrate is especially effective in reducing morbidity in underweight, stressed pigs, post-weaning.

9 Claims, No Drawings

WATER-SOLUBLE GLOBULIN CONCENTRATE FOR IMPROVING GROWTH IN ANIMALS

This application is a Continuation of U.S. patent application Ser. No. 10/613,633, filed Jul. 3, 2003 now abandoned, which is a Continuation of U.S. patent application Ser. No. 09/659,103, filed Sep. 11, 2000 now abandoned, which is a Continuation in part of U.S. patent application Ser. No. 09/258,553, filed Feb. 26, 1999 now abandoned, which is a Continuation in part of U.S. patent application Ser. No. 09/210,490, filed on Dec. 11, 1998 now abandoned, which applications are incorporated herein by reference.

FIELD OF THE INVENTION

This invention relates to a composition and method for treating piglets and other livestock. Specifically, this invention relates to the treatment of animals with a water-soluble immunoglobulin product post weaning.

BACKGROUND OF THE INVENTION

Piglets are born without the ability to fight disease. Pigs are dependent upon colostrum and later milk from the sow to provide immunoglobulins which confer passive immunity to disease for the first 2 to 3 weeks of life and help "tide them over" until their own immune systems begin functioning. The piglet's endogenous immune system begins to function and produce antibodies in response to environmental stimuli at approximately 2 weeks of age. However, the pig's immune system is not fully competent until about 5 to 6 weeks of age. Until then the pig is susceptible to many biological challenges.

Colostrum contains rapidly diminishing levels of immunologically active, large molecular weight proteins known as immunoglobulins. These immunoglobulins (Ig) possess antibody properties and enhance the pig's immunity to infection by organisms such as bacteria, viruses, and parasites. For various reasons, however, the piglet does not receive adequate amounts of immunoglobulins to impart the necessary immunity. These reasons include problems at lactation, extra large litters, litter competition, poor nursing sows, low birth weight, and sow death. This decreased immunity causes the piglets to become more susceptible to contracting various bacterial, viral, and parasitic infections, which can cause an increase in mortality from diarrhea and dehydration.

In addition to an immature immune system and a deficiency in immunoglobulins, the animals are often affected by environmental and health stress, which also weakens the animals and causes increased susceptibility to disease and various other health problems, including decreased growth and weight gain. Traditionally, these occur during the early growth and weaning period and include stress from the actual weaning process, shipping, heat, social stresses, and various challenges to the animals' health. This weakened condition is often caused by inadequate feed intake and the inability of the animal to assimilate nutritional elements from the intestine. Undigested nutrients will end up in the large intestine as a substrate for undesired intestinal bacteria flora which causes diarrhea in the animal, further complicating the post-weaning performance of the pig.

The mortality from birth to weaning in normal pig production is generally 12 to 15% but can be as high as 20 to 25% in stressed pig populations. Many of these piglets that die are the object of intense care as they are already underweight and under stress after birth. When the young pig is weaned this is an additional stress factor, especially so for the lightest pigs of the litter due to the reasons listed above.

At birth, pigs have limited enzyme systems efficient only for digestion of milk. The amount of lactase, the enzyme that breaks down and digests milk sugar, is high during the first few weeks of life but then decreases shortly after weaning. Meanwhile, proteolytic and amylolytic enzymes needed for grain digestion are not fully developed until 4 to 7 weeks of age. Thus, feed stuffs other than milk cannot be efficiently digested and absorbed until the animal is several weeks old. Further, the stress brought about by abrupt changes in diet and environment are stressful on an animal's digestive system, further aggravating the delicate balance of the system.

Current means for improving growth and reducing post-weaning morbidity in animals include the inclusion of plasma to the animals' diet. Such plasma sources have included spray-dried animal plasma (SDAP). The inclusion of spray-dried animal plasma in the diet improves feed intake, weight gain, and the efficiency of gain when compared to other protein sources such as dried skim milk, whey protein concentrate, soy protein, fishmeal, potato protein, and dried egg products. The immunoglobulin component of SDAP is recognized as the factor that improves growth in weaned pigs.

Spray-dried animal plasma is also utilized commercially in milk replacement products (milk replacers) for pigs, calves and sheep. Milk replacers are typically dry powders containing milk by-products (whey, dried skim milk, whey protein concentrate), soluble, further processed grain products (soy protein concentrate or wheat gluten), fats and oils and appropriate vitamin and mineral fortification. Research has shown that the use of milk replacers fortified with SDAP derived from whey (or colostral whey) results in faster weight gain and reduced morbidity and mortality in calves and pigs. Thomson, D. U., Weaver, Eric M. (1997), "Using Blood Proteins in Calf Milk Replacers," *Large Animal Practice*, Vol. 18, No. 6, p. 16. Large Animal Practitioner. The administration of SDAP in milk-replacers has several drawbacks, however.

First, milk replacers which include SDAP are usually provided to pigs or calves through a self-contained feeding system of some type. The feeding systems vary in complexity from a bottle with a nipple to automatic feeding devices. SDAP contains fibrinogen, a water soluble protein, which is activated by very low concentrations of calcium to form fibrin, an insoluble protein matrix. Most sources of tap water contain enough calcium to initiate the activation of the conversion of fibrinogen to fibrin. If the concentration of spray-dried animal plasma in a milk replacement product is high enough and the material is given enough time to form a protein matrix, the resulting gel will plug most feeding devices. While various anticoagulants can be used at high levels to prevent activation of the clotting process, such a level of anticoagulants may have undesirable effects on the animal either by decreasing the availability of beneficial minerals, increasing the osmotic load, or interfering with the blood clotting process in the animal.

Second, milk replacers are expensive and difficult to administer to young pigs, especially those containing significant concentrations of spray-dried animal plasma. Such products are normally prepared between 2-4 times per day in small quantities. Modern swine production is labor-intensive, and these businesses find it difficult to find and keep employees. The addition of labor-intensive production methods, i.e. feeding milk replacement products to the pigs 2-4 times daily, is often not feasible due to the lack of available farm staff.

Further, commercially available milk replacement products usually contain greater than 10% crude fat. This level of fat accumulates and plugs the water lines unless it can be completely removed from the system. Yet another major drawback with milk replacement feeding systems is that the feeding devices must be thoroughly cleaned and disinfected daily to prevent bacterial contamination.

Moreover, although the addition of SDAP to the starter diet of piglets has made it much easier to feed and manage young pigs (less than 21 days of age), it still has not proven to be completely successful in managing the light-end group of pigs, which comprise the bottom 10% of the population. This weight difference at weaning between the heaviest and lightest pigs often leads to greater differences in body weight between the heaviest and lightest pigs at the end of the nursery phase and at slaughter. Such pigs consume very little feed from 0 to 2 days post-weaning. The presence of SDAP in the feed does little to improve the health of the gut in these very small or young pigs since they do not consume adequate concentrations of feed for 2 days post-weaning. The resulting effect in these pigs is temporary gut atrophy, loss of absorptive capacity, an increase in intestinal permeability and bacterial colonization and translocation.

Elliot et al. describe formulations for milk replacement for artificial rearing of neonatal pigs. (U.S. Pat. No. 4,623,541). The formulations include purified immunoglobulins which are subsequently commingled with condensed skim milk and spray dried. The Elliot formulations are problematic, however, since the procedure for separating the immunoglobulins from the blood involves the use of high levels of ammonium sulfate. While ammonium sulfate is satisfactory for small batches of blood, it is not useful for large-scale separation operations due to problems in disposing of this environmentally hazardous compound. In addition, the Elliot process is not economical to use due to its low yields of immunoglobulin powder.

Newson et al. (U.S. Pat. No. 4,096,244) describe the administration of a composition containing active immunoglobulins to newborn piglets by feeding. An important feature of this invention is the reduction of the saline content of the blood serum to increase the palatability of the serum to the pigs. The invention also emphasizes the administration of immunoglobulins to newborn piglets by feeding and describes a feed composition similar to milk replacer. The Newson formulation is not economical to use since it is difficult to administer on a large-scale basis and does not provide for the needs of the newly-weaned pig.

There is therefore a need in the art for a supplement for young pigs (>2 days of age) which is economical and convenient to use on a large scale basis, yet also effective for administration to newly-weaned, underweight pigs.

The present inventors have now synthesized a purified, water-stable immunoglobulin product that can be administered inexpensively through the water supply of animals. The product is highly effective in increasing growth and weight gain in animals.

Accordingly, it is a primary objective of the present invention to provide a composition and method for treating animals using a water-stable, immunoglobulin product based on animal plasma.

It is a further objective of the present invention to provide a composition and method for treating animals which is effective in decreasing the adverse symptoms of stress in young animals, post-weaning.

It is a further objective of the present invention to provide a composition and method for treating animals which increases growth and weight gain.

It is still a further objective of the present invention to provide a composition and method for treating animals which is convenient and economical to administer.

It is still a further objective of the present invention to provide a composition and method for treating animals which is easy and economical to manufacture.

The method and means of accomplishing each of the above objectives as well as others will become apparent from the detailed description of the invention which follows hereafter.

SUMMARY OF THE INVENTION

The invention describes a water-stable, immunoglobulin concentrate (WSIG) which improves the health and growth rate of animals at times of stress. The invention is especially effective in improving growth and reducing morbidity in young pigs, post weaning. The WSIG is derived from animal plasma which may be treated to separate the globulin and albumin fractions. The water-stable globulin fraction is then administered to the animals through their water system.

Treatment with the globulin significantly improves health and increases the growth and weight gain in animals, especially in underweight, stressed pigs, post-weaning. The globulin composition is inexpensive to manufacture and is easy and economical to administer.

DETAILED DESCRIPTION OF THE PREFERRED EMBODIMENT

The present invention relates to a new method and composition for improving growth and weight gain in animals through the administration of immunoglobulin in the animals' water supply. Reference is often made to the use of this invention with respect to pigs, however it is to be understood that the invention is not limited to any particular animal. One of skill in the art can readily appreciate that the invention will be applicable to any food or companion animal.

Previous attempts at decreasing morbidity and mortality in young pigs have focused on the delivery of supplements, including immunoglobulin fortified supplements, via dry feed or milk prior to the weaning period. While moderately successful in reducing morbidity and mortality, these methods have many problems, including the expense and difficulties involved with the administration and use of milk replacement products. Further, light-end pigs do not benefit from the use of supplements administered through feed since they will consume primarily water during periods of stress post-weaning.

The present invention is predicated upon the discovery that the administration of immunoglobulins through the animals' water system is effective in increasing weight gain and growth in animals. This method is especially effective in highly stressed pigs that are weak with a reduced appetite. Further, unlike previous methods of supplementation, the present invention is especially effective in treating young, underweight pigs that are in a transitory starvation period post-weaning.

The composition of this invention is a plasma-based, substantially purified globulin concentrate. The term "substantially purified" refers to the fact that the globulin concentrate contains insufficient amounts of other substances that will cause the concentrate to clot or gel in water.

Similarly, the term "substantially free" of albumin refers to the fact that the globulin concentrate contains insufficient amounts of albumin to clot or gel when mixed in a highly concentrated form in water (>10% solution).

Also, the term "water-stable" refers to the fact that the globulin concentrate of this invention does not gel, precipitate, or clot. Instead, the water-stable product is a fluid with free-flowing solution characteristics.

Nutritional supplements, including SDAP, have generally been administered through the animal's feed or as part of milk replacement therapy. Blood plasma itself gels in water. Now, using the applicants' globulin separation method, the globulin can be administered inexpensively through the animals' water. The globulin concentrate of the present invention is stable in water, and therefore does not clog the lines of the animal's water system. Further, in contrast to spray-dried animal plasma and other feed and milk replacement supplements, Applicants' globulin concentrate does not need to be placed in the food supply numerous times per day, thereby decreasing labor costs.

The globulin concentrate of the present invention can be administered to animals during all stages of their life cycles to improve their health and nutrition, but is more effective in periods of stress, and is especially effective in young, stressed pigs, post-weaning. These pigs are usually weak from both disease and lack of appetite. The consumption of immunoglobulin from the water improves the short-term enteric health of the animal which promotes feed and water intake. The provision of immunoglobulin in the water ensures the short-term protection of the pig's enteric health.

Swine producers can use the globulin concentrate of the present invention to improve the health and growth rates of pigs. The product is efficacious, especially in young stressed, pigs, cost-effective, and a labor saving tool in the management of pigs. The commercial applications of this invention are many and range from the use of the concentrate to more successfully wean large groups of pigs at very young ages (<10 days of age) to the administration of the product to weaned pigs in traditional swine production systems to overcome typical health challenges. Swine units have progressively grown in size and there is less management time allotted to the care of individual pigs. Health management is critical in minimizing disease outbreaks since such outbreaks are expensive in terms of medication cost and management time. This invention is successful in promoting the maintenance of enteric health by supplying an appropriate, adequate source of gastrointestinal protection to the animals.

The immunoglobulin concentrate and water delivery method is also effective in protecting the gastrointestinal health of other stressed animals, including cattle, horses, and poultry. Stress such as mild to severe starvation, shipping, surgery, socialization, corticosteroid treatment, intentional weight reduction, force molting (poultry), physical disability, and birthing, all can result in a reduction in feed intake and breakdowns in gastrointestinal health. The opportunity for disease is decreased through the administration of the present water-soluble immunoglobulin concentrate.

The immunoglobulin concentrate of the present invention is derived from animal blood. The source of the blood can be from any animal that has blood which includes plasma and immunoglobulins. For convenience, blood from beef, pork, and poultry processing plants is preferred. Anticoagulant is added to whole blood and then the blood is centrifuged to separate the plasma. Any anticoagulant may be used for this purpose, including sodium citrate and heparin. Persons skilled in the art can readily appreciate such anticoagulants. Calcium is then added to the plasma is to promote clotting, the conversion of fibrinogen to fibrin. This mixture is then centrifuged to remove the fibrin portion.

As described above, it is the fibrin portion which combines with calcium from the water source to gel and clog water lines. Once the fibrin is removed from plasma resulting in serum, the serum can be used as a principal source of Ig. Alternatively, one could also inactivate this portion of the clotting mechanism using various anticoagulants.

In addition, one could simply inject the water-stable plasma into the water as the immunoglobulin source. Either serum or plasma may be used as an immunoglobulin source in the globulin concentrate product. The further processing to concentrate immunoglobulin simply ensures fewer problems with line obstruction because less protein will be injected into the line.

The defibrinated plasma is next treated with an amount of salt compound or polymer sufficient to precipitate the albumin or globulin fraction of the plasma. Examples of phosphate compounds which may be used for this purpose include all polyphosphates, including sodium hexametaphosphate and potassium polyphosphate. The globulin may also be isolated through the addition of polyethylene glycol or ammonium sulfate. For reasons of convenience and economy, the polyphosphate compounds are preferably added to the plasma in a concentration of about 0.5-1% by weight of the plasma.

Following the addition of the phosphate compound, the pH of the plasma solution is lowered to a range of between 3.5-4.5 to stabilize the albumin precipitate. The pH should not be lowered below 3.5, as this will cause the proteins in the plasma to become damaged. The preferred pH range is 3.5-4.0, with 3.95 being most preferred. Any type of acid can be used for this purpose, so long as it is compatible with the plasma solution. Persons skilled in the art can readily ascertain such acids. Examples of suitable acids are HCl, acetic acid, $H_2SO_4$, citric acid, and $H_2PC_4$. HCl is preferred, and 2N HCl is most preferred. The acid is added in an amount sufficient to lower the pH of the plasma to the designated range. Generally, this amount will range from a ratio of about 1:4 to 1:2 acid to plasma. The plasma is then centrifuged to separate the globulin fraction from the albumin fraction.

The next step in the process is to raise the pH of the globulin fraction with a base until it is no longer corrosive to separation equipment. Acceptable bases for this purpose include NaOH, KOH, and other alkaline bases. Such bases are readily ascertainable by those skilled in the art. NaOH is the preferred base, and a 10% solution of NaOH is most preferred. The pH of the globulin fraction is raised until it is within a non-corrosive range which will generally be between 5.0 and 9.0. The preferred pH range is 7.0-8.0, with 7.5 being most preferred. The immunoglobulin fraction is then preferably microfiltered to remove any bacteria that may be present.

The final immunoglobulin concentrate can optionally be spray-dried into a powder. The powder allows for easier packaging and the product remains stable for a longer period of time than the raw globulin concentrate in liquid or frozen form. The immunoglobulin concentrate powder has been found to contain approximately 35-50% IgG. The immunoglobulin concentrate is then mixed with serum concentrate and other compounds to improve wettability.

The globulin concentrate is administered to the animal by placing it in the animal's water system via a stock solution and a liquid dispenser. The globulin composition readily dissolves in water and remains stable in a highly-concentrated solution that does not obstruct the water line. While animals receive benefit from any amount of globulin composition placed in their water source, the concentration of globulin composition in the water should be at least 0.1% by weight. The response to the product is titratable, meaning a greater response is observed with a higher concentration so much higher levels of globulin concentrate can be added. The concentration of globulin can be increased until the water becomes saturated with globulin, i.e. the globulin can no longer be dispersed within the water. Various concentrations of stock solutions and/or injection rates may be used to alter the concentration of immunoglobulin in the water.

For economy and efficiency and to achieve best results in stressed pigs, the globulin composition should be dispersed in the water in a concentration of from about 0.375 to about 3.0% by weight. The concentration of IgG in the water in this concentration ranges from approximately 0.1-0.75% by weight.

A preferred water dispenser for use with this invention is manufactured by Dosatron® and is sold as the Proportional Non Electric Liquid Dispenser. The dispenser is installed directly on the water supply line. The dispenser is activated by water pressure. As the water passes through the dispenser it takes up the designated percentage of concentrate to deliver to the animals.

The globulin concentrate can be administered to the animal at any stage of the animal's life. However, as a practical matter it will be most frequently used in young pigs prior to the stage when they begin consuming feed since this is the group of animals that have shown the greatest response to the treatment. The concentrate is most advantageously used during times when the animals are most stressed. As already described, the globulin concentrate is especially effective in animals post weaning during the transient starvation period when they are not yet consuming feed. The animal drinks the globulin-fortified water and, with improved health, begins to eat and to drink larger quantities of the water. As the animal continues to drink, the globulins from the water help protect the animal from disease by providing additional protective support to the mucosal barrier. The additional protection helps the animal overcome the negative effects of stress, including leaky gut syndrome and diarrhea. Noticeable improvements in growth will occur with oral administration of 75 mg immunoglobulin/kg body weight or 0.5 g immuno-globulin/hd/day. However, concentrations that will provide 375 mg immunoglobulin/kg body weight or >2.5 g/hd/day are most effective.

The globulin concentrate may also be administered with certain additives or nutrients, such as carbohydrates, vitamins and minerals, that are added to the water directly or mixed in with the concentrate prior to adding to the water. The only requirement is that the additives also be water soluble and compatible with the immunoglobulin concentrate. Such additives can be readily ascertained by those skilled in the art. An example of such a composition is included (Table 2). This composition is then agglomerated to improve wettability.

In tests involving the globulin concentrate, the administration of the product to pigs through water reduced the frequency of medication administration and the severity of disease outbreaks.

The following examples are offered to illustrate but not limit the invention. Thus, they are presented with the understanding that various formulation modifications as well as method of delivery modifications may be made and still be within the spirit of the invention.

Example 1

Effect of Immunoglobulin Concentrate on Young Weaned Pigs

Porcine immunoglobulin was substantially purified from porcine plasma using the previously described procedures. The porcine immunoglobulin concentrate was spray-dried and analyzed for porcine IgG content. In powder form, the product contained by analysis 45% IgG. This powder was then reconstituted with tap water and the pH reduced to approximately 4.5 with citric acid to produce a 30% w/w stock solution. This stock solution was then injected into the water line in a ratio of 1 part per 100 parts water which was used as the sole water source for 6 pens of 24 pigs/pen in the trial. The product was injected into the water line for a period of one week. The control group (six pens of 24 pigs/pen) were provided with water injected with an acidified stock solution (as above). Pig weights were measured initially and at the end of the 7 day trial period. The number of pigs medicated during the week was recorded for both the control and treated (+Ig) groups:

TABLE 1

| Body Weight (kg) | Control | +Ig |
|---|---|---|
| Initial Weight | 6.02 | 5.92 |
| Final, d 7* | 7.64 | 7.61 |
| ADG, g/d | 231 | 241 |
| Medication, % of pigs | 12.5% | 4.0% |

*Final body weights represent an average body weight for the pen of pigs. Pigs were removed from the pen for intensive care when necessary.

Table 2 sets forth the composition of the water-stable globulin concentrate used in the study:

TABLE 2

| Ingredient | As-is, % |
|---|---|
| Serum concentrate | 52.21 |
| Immunoglobulin concentrate | 24.28 |
| Lactose | 15.00 |
| Fructo-oligosaccharide | 5.00 |
| Potassium chloride | 1.66 |
| Lecithin | 1.00 |
| DL-methionine | 0.86 |
| Total | 100.0 |

Example 2

Effect of Immunoglobulin Concentrate on Young Weaned Calves 120 calves 8.9 days of age were fed calf milk replacer (CMR) for 42 days and commercial calf starter (CS) and water ad lib for 56 days. In the first 15 days of the study and prior to each feeding, either bovine-derived immunoglobulin concentrate or placebo was added to the mixing tank (to 1.9 l CMR) at the following rates:

60 g for 5 days (0.51% IgG);
45 g for 5 days (0.38% IgG); and
30 g for 5 days (0.25% IgG).

The body weight, feed intake, efficiency, and health of the calves were then measured using fecal scores and scours, use of electrolytes and Ab, mortality, blood IgG, and Hct (day 0). The results are set forth in Tables 3-6 below:

TABLE 3

| Body Weight | | |
|---|---|---|
| Body weight (kg) | | |
| No Gammulin | Gammulin | Day of Study |
| 47.3 | 46.3 | 0 |
| 54.7 | 53.7 | 28 |
| 71.2 | 72.3 | 56 |

TABLE 4

Body Weight

| Body Weight Increase (g/d) | | | |
|---|---|---|---|
| No Gammulin | Gammulin | Days of Study | Percent Gain |
| 264 | 262 | 0-28 | — |
| 589 | 665 | 29-56 | +12.9% (P < 0.07) |
| 426 | 463 | 0-56 | +8.7% (P < 0.10) |

TABLE 5

Efficiency

| | CMR (g/d) | CS (g/d) | G:F g/kg |
|---|---|---|---|
| Gammulin | 390 | 486 | 422 |
| No Gammulin | 390 | 525 | 459 |

TABLE 6

Health

| | Fecal Scores* | Scours (%) $P < 0.07$ (−23%) | Electrolytes (%) $P < 0.10$ (−39%) | Ab (%) (−50%) |
|---|---|---|---|---|
| Gammulin | 1.6 | 12.4 | 4.4 | 2.2 |
| No Gammulin | 1.6 | 9.6 | 2.7 | 1.1 |

*1 = normal to
4 = severe scours

Conclusions

Overall, the delivery of immunoglobulins to the calves had no significant effect on mortality (1 calf—0.8% mortality), intake of calf milk replacer or starter, or intake of fat or protein. Further, the palatability of all the diets was excellent. The study demonstrates that immunoglobulins delivered through the water can significantly enhance the growth, feed efficiency, and health of weaning calves.

Example 3

Effect of Immunoglobulin Concentrate on Chicks

Porcine immunoglobulin concentrate was substantially purified from porcine plasma using polyphosphate precipitation. The porcine immunoglobulin concentrate contained by analysis 36% IgG by weight. A 1% solution of the porcine immunoglobulin concentrate was prepared fresh each morning and acidified to pH 4.6 using 25% phosphoric acid to control bacterial growth. This solution was the only source of water to the birds in the immunoglobulin treatment. To determine the effectiveness of acidification in controlling bacterial growth in the immunoglobulin solution, samples of the solution immediately after mixing and after 24 hours were taken. Control birds received water that was not acidified.

Diets

Both the Control and Immunoglobulin groups received Purina® Gamebird Chow ad lib during the experiment. This diet meets all the nutritional requirements of chickens and is non-medicated.

Animals

Eighty-four, mixed sex white leghorn chickens were used in this experiment. The chicks were one day old at the beginning of the experiment. The chicks were randomly assigned to 4 cages (21 chicks per cage) in a battery brooder. The birds were weighed at the start of the experiment and on days 4, 7, 14 and 21. Feed consumption was measured during the third week of the experiment.

Results

Viable Bacteria in Immunoglobulin Solution

The immunoglobulin solution used in this experiment was adjusted to pH 4.6 to control bacterial growth. The number of viable bacteria in the solution initially and after 24 h in the trough are shown in Table 7. There was a large increase in the number of bacteria in the immunoglobulin solution during the 24 h period. The applicants tried adjusting the pH of the water to 4.2 during one day of the experiment, but this decreased the number of bacteria by less than 1 log. The dominant organisms were gram-negative bacilli and cocci. It is suspected that most of these organisms may be fecal coliforms such as *E. coli*, *Enterobacter cloacae* and *Enterobacter aerogenes* since the water troughs were usually contaminated with chicken feces by the end of the feeding period. It is also possible that some of these bacteria may belong to spoilage organisms such as *Pseudomonas* spp.

TABLE 7

| | Total Viable Bacteria (CFU/mL) | |
|---|---|---|
| Starting pH | 0 h | 24 h |
| 4.6 | $4.3 \times 10^3$ | $2.1 \times 10^8$ |
| 4.2 | $9.2 \times 10^2$ | $7.3 \times 10^7$ |

Chick Growth and Feed Consumption

During the first week of the experiment, there were no significant differences in average daily gains between the Control and the Immunoglobulin treatment groups (P>0.05) (Table 7). However, during the second and third weeks of the experiment the Immunoglobulin treatment chickens gained significantly faster than did the controls (P<0.05). There were no significant differences in feed consumption or feed to gain ratios between the two groups during the third week of the experiment (P>0.05) (Table 7).

Conclusions

Immunoglobulins delivered through the water can significantly enhance the growth of laying-type chickens.

Example 4

Preferred Manufacturing Method for Globulin Concentrate

The following illustrates a preferred method of manufacturing the globulin concentrate of the present invention:

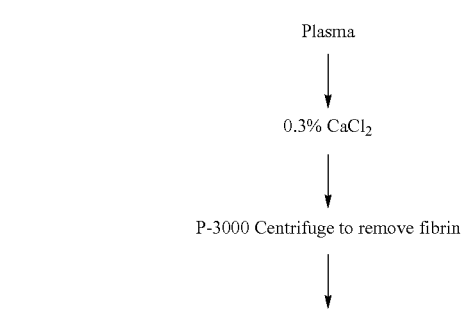

Plasma
↓
0.3% CaCl$_2$
↓
P-3000 Centrifuge to remove fibrin
↓

-continued

Allow any foam to dissipate
Filter sock 60 mesh

↓

Add 1% Hexameta Phosphate (granular form) by wt. to serum
This is made up as a stock solution
(1 lb to 1.7 lbs hot water) (≈ 230 lbs solution)
and added as a solution to the serum

↓ pH is adjusted to 3.9-3.96 range (3.95 is target),
with a 2N HCl solution
This is done as a slow time dependent addition
(approx 718.5 lbs/1000 gal)
After pH adjustment, allow 1 hour for reaction
completion while stirring

↓

Centrifuge Alpha Laval 717 feed rate approx 18 gal/min
To determine rate of feed and discharge, use microcentrifuge
tubes to determine solids for discharge rate
(use 10,000 g x 10 min),

↓

Wt. Supernatant
Wt. Liquid
Determine % solids

↙ ↘

Globulin Fraction

This pH and form is stable for
several days for SPC's and can
be used to allow accumulation
of material for spray dryer

↓

Raise pH to 7.5 with 10% NaOH
(≈ 186.3 lbs) - microfiltration
to remove any bacteria

↓

Dialyze 20,000 molec. wt.
membranes to conductivity of
1.5 ms/cm at 12 g/dl protein

↓

Concentrate and spray dry
294° C. inlet and 95° C. outlet

↓

Albumin Fraction

This form is stable for
several days so accumula-
tion for the spray dryer
is possible

↓

Dilute thick slurry by 50%
with distilled water
before processing
Raise pH to 8.0 with 10%
NaOH (≈ 116 lbs) slowly -
Do not burn proteins
Microfiltration to remove
any bacteria

↓

Dialyze (20,000 m.w.
membranes) to conduction
of 1.5 ms/cm at 12 g/dl
protein level

↓

Concentrate and spray dry
294° C. inlet and 95° C.
outlet

↓

-continued

| Analyze spray dried powder | | Analyze spray dried powder | |
|---|---|---|---|
| T.P | Phoslip | T.P | Phosphorus |
| Alb. | Phosphorus | Alb. | Calcium |
| IgG | Calcium | IgG | Na |
| Chol | Na | Chol. | Cl |
| Trig | Cl | Trig | K |
| K | | Phoslip | |

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of improving weight gain and growth, while decreasing morbidity and mortality in a pig, cow or horse comprising:
   providing water supplemented with an effective amount of a water miscible and stable immunoglobulin concentrate to the pig, cow or horse, wherein the source of the concentrate is blood plasma from which the fibrin has been separated, wherein the concentrate comprises at least 15% by weight IgG, wherein the concentrate is not a component of a milk replacer,
   and wherein the pig, cow or horse is at any stage of life from weaning up to about six weeks of age;
   so as to improve weight gain and growth, while decreasing morbidity and mortality in the pig, cow or horse wherein the immunoglobulin concentrate is dispersed in the water in a concentration of from about 0.375 to about 3% by weight and the dispersion yields a concentration of IgG in the water about 0.1-0.75% by weight.

2. The method according to claim 1 wherein the water is provided to a pig.

3. The method according to claim 1 wherein the water is provided to a cow.

4. The method according to claim 1, wherein the water is provided to a calf.

5. The method according to claim 2 wherein the pig is underweight.

6. The method according to claim 1 wherein the immunoglobulin concentrate comprises about 35-50% IgG.

7. The method according to claim 1 wherein the immunoglobulin concentrate is provided in a dose of 0.5 g immunoglobulin/hd/day or more.

8. The method according to claim 1 wherein the immunoglobulin concentrate is provided with one or more additives or nutrients selected from the group consisting of water-soluble carbohydrates, vitamins, and minerals.

9. The method according to claim 1 wherein the pig, cow or horse has not yet begun to consume feed.

* * * * *